(12) United States Patent
Tsukada et al.

(10) Patent No.: US 7,525,308 B2
(45) Date of Patent: Apr. 28, 2009

(54) MAGNETIC DETECTING DEVICE AND MATERIAL IDENTIFYING DEVICE

(75) Inventors: Keiji Tsukada, Okayama (JP); Toshihiko Kiwa, Okayama (JP)

(73) Assignee: Okayama University, Okayama (JP)

( * ) Notice: Subject to any disclaimer, the term of this patent is extended or adjusted under 35 U.S.C. 154(b) by 305 days.

(21) Appl. No.: 11/632,125

(22) PCT Filed: Jul. 7, 2005

(86) PCT No.: PCT/JP2005/012966

§ 371 (c)(1), (2), (4) Date: Feb. 7, 2007

(87) PCT Pub. No.: WO2006/009048

PCT Pub. Date: Jan. 26, 2006

(65) Prior Publication Data

US 2008/0074109 A1    Mar. 27, 2008

(30) Foreign Application Priority Data

Jul. 16, 2004    (JP)    ............................. 2004-209703

(51) Int. Cl.
*G01R 33/12* (2006.01)
(52) U.S. Cl. .................. 324/243; 340/551; 324/235
(58) Field of Classification Search ................ 324/228, 324/235–243, 252, 260; 340/551, 572.1–572.2
See application file for complete search history.

(56) References Cited

U.S. PATENT DOCUMENTS 5,689,184 A * 11/1997 Jeffers et al. ................ 324/243
6,853,194 B2 * 2/2005 Nelson et al. ............... 324/329
2005/0253711 A1 * 11/2005 Nelson ........................ 340/552

FOREIGN PATENT DOCUMENTS

| JP | B2 64-002904 | 1/1989 |
| JP | Y2 04-011187 | 3/1992 |
| JP | A 05-093782 | 4/1993 |
| JP | A 11-118766 | 4/1999 |
| JP | 2004117227 A * | 4/2004 |
| JP | 2004151064 A * | 5/2004 |

* cited by examiner

*Primary Examiner*—Jay M Patidar
(74) *Attorney, Agent, or Firm*—Oliff & Berridge, PLC (57) ABSTRACT

The present invention discloses a magnetic detecting device comprising an apply coil 1 for generating an alternate magnetic field of variable frequency and a power source 2 for the apply coil; a magnetic sensor 5 for detecting a change in the magnetic field induced by a test object 9 placed at a distance from a surface of said apply coil and toward said test object, said magnetic sensor being provided with a cancel coil 6 for canceling a magnetic field generated at the position of the magnetic sensor by a direct magnetic field and/or said apply coil; a measurement circuit 7 for the magnetic sensor for measuring a detection signal of said magnetic sensor; a lock-in amplifier circuit 8 for detecting an output of said measurement circuit for the magnetic sensor into two signals having the same frequency as that of said apply coil and phases different from each other by 90 degrees; and an analysis means 10 for analyzing a phase change of the output of said magnetic sensor 5 using an output signal from said lock-in amplifier circuit 8.

8 Claims, 6 Drawing Sheets

MAGNETIC DETECTING DEVICE AND MATERIAL IDENTIFYING DEVICE

TECHNICAL FIELD

The present invention relates to a device for applying an alternate magnetic field to a test object and detecting response characteristics thereof using a magnetic sensor.

RELATED ART

A metal detector is known as a device for applying an alternate magnetic field to examine the response characteristics. The metal detector comprises a search coil that generates an alternate magnetic field to generate an eddy current on a metal surface of the test object, which in turn generates a magnetic field repulsive to the applied magnetic field. Since this magnetic field changes an electromotive force in response to changes in the magnetic flux penetrating through the search coil, as may be represented using Faraday's law of electromagnetic induction, existence of metal can be detected by measuring the changes in a signal. Also known are methods of nondestrucive inspection such as a method for inspecting a defect in a steel pipe or a wire rope by generating an eddy current in the same manner as in the case of the metal detector. Among applied examples of the metal detector are a metal detection gateway for preventing dangerous articles from being carried in for the purpose of terrorism prevention or crime prevention and a device for detecting a piece of metal, a needle for example, having been misplaced during manufacture in articles such as meat or clothes.

Among various kinds of metal materials, metals having superior electrical conductivity such as copper and ferromagnetic materials such as iron and chromium are easy to detect, while stainless-steel or the like, having lower electrical conductivity and not being ferromagnetic, is difficult to detect. There is also generated an eddy current in meat, though not being a metal, because of its electrical conductivity. When different kinds of materials are nixed, they can be separated to a certain extent by capturing a change of the phase of the signal having been detected with a magnetic sensor as compared to that of applied magnetic field According to Japanese Patent Publication No. 3122572 (Patent Reference 1), a metal signal is detected by putting a product, a food product for example, on a belt conveyor, applying an alternate current in the similar way as in the case of a metal detector, measuring a plurality of signals having different phases by means of a search coil and obtaining a time change in the phases. Further, as for ferromagnetic metals such as iron, magnetism generated from the material may be directly detected by means of a magnetic sensor, without using the eddy current method. In this method, the test object is magnetized using an applying coil, and the metal having been magnetized with an applied magnetic field is then detected in a different place by means of a magnetic sensor. Since the magnetic field generated from the magnetized metal is a direct one and not an alternate one, the magnetic field cannot be detected with a coil.

According to Japanese Patent Application Laid-Open No. 2004-151064 (Patent Reference 2) and *Potentiality of Applied Measurement using Superconducting Quantum Interference Device (SQUID)* by Saburo TANAKA, *Oyo Buturi*, Vol. 72-8, 2003, pp. 1039-1045 (Nonpatent Reference 1), there is disclosed a detecting device for detecting a minute metal piece having been misplaced in food by means of a SQUID, a magnetic sensor. With highest sensitivity. Besides methods as described above of detecting a magnetized ferromagnetic material, there is also disclosed in Japanese Patent Application Laid-Open No. 2004-117227 (Patent Reference 3) a method of capturing a change in an applied magnetic field caused by ferromagnetic material using a magnetic sensor. With the method of Patent Reference 3, it is possible to capture a change in the magnetic field caused by a test object even in the case of a nonmagnetic material. Results of an analysis of each of signals of a nonmagnetic material and a magnetic material may be displayed separately or simultaneously.

Further, there is disclosed in Japanese Patent Application Laid-Open No. H7-244165 a method of separating a signal of the nonmagnetic material from a signal of the magnetic material, in which the signal of the nonmagnetic material is captured using a filter that only transmits magnetic signals included in an output of the magnetic sensor having the same frequency as that of the applied magnetic field, whereas a magnetic signal generated from the magnetic material is captured using a filter that transmits signals having other frequencies than that of the applied magnetic field.

Patent Reference 1: Japanese Patent Publication No. 3122572
Patent Reference 2: Japanese Patent Application Laid-Open No. 2004-151064
Patent Reference 3: Japanese Patent Application Laid-Open No. 2004-117227
Patent Reference 4: Japanese Patent Application Laid-Open No. H7-244165
Nonpatent Reference 1: *Potentiality of Applied Measurement using Superconducting Quantum Interference Device (SQUID)* by Saburo TANAKA, *Oyo Buturi*, Vol. 72-8, 2003, pp. 1039-045

DISCLOSURE OF THE INVENTION

Problems to be Solved

With a method of measuring a phase change as a means for analyzing a complex test object such as meat containing a misplaced metal piece, results of measurement cannot be obtained instantaneously because there is a need for measuring the complex test object flowing on a belt conveyor for a certain length of time to obtain a time change. As a result, this method cannot be applied, for example, to objects that are not being conveyed. Accordingly, the method of measuring a time change in phase cannot be applied to objects that cannot be conveyed at a constant velocity, for example a complex object including a human body, a coin in a moneybag and a dangerous article such as a knife in the case of a metal detection gateway for the purpose of crime prevention.

Further, there is a problem in the method for detecting a dangerous article by magnetizing ferromagnetic material such as iron that materials which are not supposed to be detected are also magnetized. For example, a magnetic card will be made unusable. Therefore, measurement by means of magnetization can be applied to limited cases. In a method of measuring a change in the applied magnetic field caused by a test object by means of a magnetic sensor without any magnetization, signals of a magnetic material and a nonmagnetic material such as aluminum are analyzed with a magnetic sensor. However, leaving out of consideration response characteristics for frequency changes in the applied magnetic field, an analysis cannot be made, for example, of a complex object containing magnetic and nonmagnetic materials.

Further, in a method of using a search coil as a magnetic sensor, the detection accuracy increases as the frequency becomes higher. For this purpose, a frequency of some kHz to some hundreds kHz is used for metal detectors. However, there is a problem at issue of effects of high frequency magnetic fields being applied to a human body. Although the effects of high frequency magnetic fields have not yet been quantified, there has been found a negative impact, for example, of heat generated with an eddy current in a human body induced by a high frequency magnetic field. Thus, it has been required to conduct measurement using a magnetic field of lower frequency.

Further, since a positional relation of the magnetic sensor, the apply coil and the test object is uncertain, there is a difficulty in detection with the use of a magnetic sensor if the distance between the test object and the magnetic sensor is large and the signal is weak. None of the detecting devices described above comprises a means for measuring a distance between a test object and a search coil or a magnetic sensor. Therefore, it has remained impossible to determine whether a change in intensity of the signal is caused with distance or with magnetic response characteristics of the measuring material.

Means for Solving the Problems

The present invention is intended to solve the above-described problems. A magnetic detecting device according to a first aspect of the present invention comprises:

an apply coil for generating an alternate magnetic field of variable frequency and a power source for the apply coil, a magnetic sensor for detecting a change in a magnetic field induced by a test object placed at a distance from a surface of said apply coil and toward said test object, said magnetic sensor being provided with a cancel coil for canceling a magnetic field generated at the position of the magnetic sensor by a direct magnetic field and/or said apply coil, a measurement circuit for the magnetic sensor for measuring a detection signal of said magnetic sensor, a lock-in amplifier circuit for detecting an output of said measurement circuit for the magnetic sensor into two signals having the same frequency as that of said apply coil and phases different from each other by 90 degrees and an analysis means for analyzing a phase change of the output of said magnetic sensor using an output signal from said lock-in amplifier circuit.

A second aspect of the present invention relates to the magnetic detecting device according to the first aspect, further comprising a distance measurement means for measuring a distance between said test object and any one of said apply coil or said magnetic sensor.

A third aspect of the present invention relates to the magnetic detecting device according to any one of the first and second aspects, wherein the area of said cancel coil is made small so as not to influence magnetic detection by said magnetic sensor.

A fourth aspect of the present invention relates to the magnetic detecting device according to any one of the first to third aspects, wherein a composite magnetic field of a plurality of frequencies is generated at said apply coil by said power source for the apply coil, and said lock-in amplifier circuit is provided for each of the plurality of frequencies.

A fifth aspect of the present invention relates to the magnetic detecting device according to any one of the first to fourth aspects, wherein a pair of facing apply-coils are provided as said apply coil, and said test object is placed between said pair of facing apply coils.

A sixth aspect of the present invention relates to the magnetic detecting device according to the fifth aspect, wherein a plurality of said magnetic sensors for measuring a magnetic component in a direction perpendicular to the direction of the axis of said facing apply coils are provided.

A seventh aspect of the present invention relates to the magnetic detecting device according to any one of the first to sixth aspects, wherein any one of a hall element, a magnetoresistive element, a magnetic impedance effect sensor, a flux gate or a superconductive quantum interference device is used as said magnetic sensor.

A eighth aspect of the present invention relates to a material identification device for identifying a structure material contained in said test object using the magnetic detecting device according to any one of the first to seventh aspects.

EFFECTS OF THE INVENTION

According to the first aspect of the present invention, it is possible to detect, by means of a lock-in amplifier circuit, an output from the measurement circuit for the magnetic sensor into two signals having the same frequency as that of the apply coil and phases different by 90 degrees from each other. Thus, the output can be separated into two parts, a magnetic response from the ferromagnetism and a response from an eddy current. Since an induced electromotive force V in an electrical conductor generated by an alternate magnetic field is proportional to a time rate of change of a magnetic flux $\Phi(d\Phi/dt)$, V can be represented as follows, where $\Phi=\Phi_0 \exp(i\omega t)$ (i: an imaginary unit):

$$V = -i\omega\Phi_0 \exp[i\omega t] = \omega\Phi_0 \exp[i(\omega t - \pi/2)]$$

Thus, the phase of an eddy current I (=V/R, R: resistance) induced by the above described induced electromotive force V is shifted by 90 degrees ($\pi/2$) from the above described alternate magnetic field. In other words, the intensity of the magnetic field H generated at the position of the magnetic sensor by the above described current is represented as H=I/2r where the eddy radius of the eddy current is r. Thus, the phase of a magnetic response from the electrical conductor is shifted by 90 degrees because of the phase shift of the eddy current. Accordingly, the above described magnetic response containing magnetic signals generated in different ways as described above can be separated into two signals having phases different by 90 degrees from each other. Thus, various information can be obtained from the magnetic response characteristics of the above described test object.

Further, while the frequency of the alternate magnetic field was fixed in the prior art, the frequency may be variable in the present invention. Even if the test object contains a complex of a magnetic material and a nonmagnetic material, the complex object can be identified by measuring a change in the response characteristics in response to a change in frequency. Thus, it is not necessary to convey the test object to measure a time change in phase, and material identification of the test object in the magnetic field can be made in a moment of time. In addition, it is possible to confine magnetic changes to be detected to those caused by a magnetic response from the test object by detecting the output from the measurement circuit for the magnetic sensor using the same frequency as that of the apply coil.

Further, the magnetic sensor can be used even in the case where the signal of magnetic response characteristics is weak and of low frequency, because the above described magnetic sensor is placed near the test object. Since the magnetic sensor responds to a direct magnetic field, an environmental magnetic field such as the terrestrial magnetism may cause a noise louder than the signal. However, the noise component can be effectively removed by providing a cancel coil at a position adjacent to the magnetic sensor. Although the applied alternate magnetic field may cause a noise at the position of the magnetic sensor, the above described noise component can be removed in a dramatically improved manner by providing a cancel coil for the alternate magnetic field.

When measuring magnetic response characteristics of the test object, the magnetic change varies depending on the distance between the apply coil and the test object and the distance between the magnetic sensor and the test object. According to the second aspect of the present invention, detection can be made with higher repeatability because a distance measurement means for measuring the distance between the apply coil and the magnetic sensor is provided. Further, since distance information can be obtained as well as magnetic response information, there is no need to continuously measure the phase change of the magnetic signal, and the structure materials contained in the test object can be identified in a moment of time based on the above described magnetic response.

According to the third aspect of the present invention, it is possible to prevent a magnetic field induced by the cancel coil from being applied to the test object, by making the area of said cancel coil small so as not to influence the magnetic detection with the use of said magnetic sensor. A preferable ratio of coil areas, which can be obtained by dividing the area of the cancel coil by the area of the apply coil, is a tenth or less. In order to increase the rate of decay of the magnetic field as a function of the distance from the cancel coil, a more preferable ratio of coil areas is a fiftieth. Most appropriately, the rate of coil areas is a hundredth or less, with which the rate of decay of the magnetic field as a function of the distance from the cancel coil increases dramatically, making the influence of the cancel coil upon the test object negligible.

According to the fourth aspect of the present invention, since a composite magnetic field of a plurality of frequencies is generated, and an output of the magnetic sensor is phase-detected using a plurality of frequencies instead of changing the frequency of the applied magnetic field, magnetic responses of the test object for two frequencies can be measured simultaneously without switching between the frequencies. Therefore, measurement of the frequency characteristics of a magnetic response may be speeded up dramatically.

According to the fifth aspect of the present invention, a uniform distribution of the applied magnetic field covering a wide range can be applied to the test object because a pair of facing apply coils are provided as the apply coil. Therefore, a uniform magnetic signal can be obtained from the test object and the magnetic response characteristics can be measured with high accuracy.

According to the sixth aspect of the present invention, magnetic response characteristics at different parts of the test object can be measured, because a plurality of the above described magnetic sensors for measuring a magnetic component in a direction perpendicular to the direction of the axis of the above described facing apply coils are provided. Therefore, information of the structure materials contained in the test object can be obtained three-dimensionally, and a three-dimensional structure, as well as material characteristics, can be measured.

According to the seventh aspect of the present invention, a magnetic response can be detected by applying an alternate magnetic field of low frequency, because a hall element a magnetoresistance element, a magnetic impedance effect sensor, a flux gate or a superconductive quantum interference device is used as said magnetic sensor. When any one of a magnetoresistance element, a magnetic impedance effect sensor, a flux gate and a superconductive quantum interference device is preferably used, a magnetic response can be detected with an alternate magnetic field of low frequency in the range of 1 kHz to less than some Hz. If a superconductive quantum interference device is more preferably used as a magnetic sensor, a magnetic response of low frequency and low intensity can be measured with drastically improved accuracy. Therefore, it is possible to reduce influences imposed on a human body or other living things and various types of products or electronic equipments comprising ferromagnetic material as a component thereof such as a magnetic card, a personal computer or a monitor.

According to the eighth aspect of the present invention, a magnetic response of the test object can be measured with high sensitivity with the used of the magnetic detecting device according to any one of the first to the seventh aspects. Therefore, the structure materials contained in the test object can be identified with high accuracy. For example, security check at public facilities such as an airport or a sports arena, detection of landmines buried in the ground, detection of a foreign matter in food or detection of a steel frame buried in concrete can be made with high accuracy. Further, because an alternate magnetic field of low frequency is used to identify the structure materials contained in the test object, the device may be used as a medical inspection equipment. For example, metal powder having invaded the lung in the case of pneumoconiosis can be detected. Further, even a current in the body induced when an electromagnetic wave of low frequency is irradiated to a human body can also be detected.

1 apply coil
2 power source for the apply coil
3 current source
4 signal sender
5 magnetic sensor
6 cancel coil 7 measurement circuit for the magnetic sensor
8 lock-in amplifier circuit
9 test object
10 analysis means
11 amplifier
11-3 amplifier
11-4 amplifier
12-1 phase detection circuit
12-2 phase detection circuit
12-3 phase detection circuit
12-4 phase detection circuit
12-5 phase detection circuit
12-6 phase detection circuit
13 90 degree phase shift
14-1 low-pass filter
14-2 low-pass filter
15 in-phase output terminal
15-3 in-phase output terminal
15-4 in-phase output terminal
16 90-degree phase output terminal
16-3 90-degree phase output terminal
16-4 90-degree phase output terminal
17 high-pass filter
20 apply coil magnetic field cancel coil
21 direct magnetic field cancel coil
22 distance measurement means
30-1 facing apply coil
30-2 facing apply coil
31-1 facing apply coil
32-2 facing apply coil

BEST MODE FOR CARRYING OUT THE INVENTION

Preferred embodiments of the present invention will be explained hereinafter with reference to figures.

Embodiment 1

Figure 1:
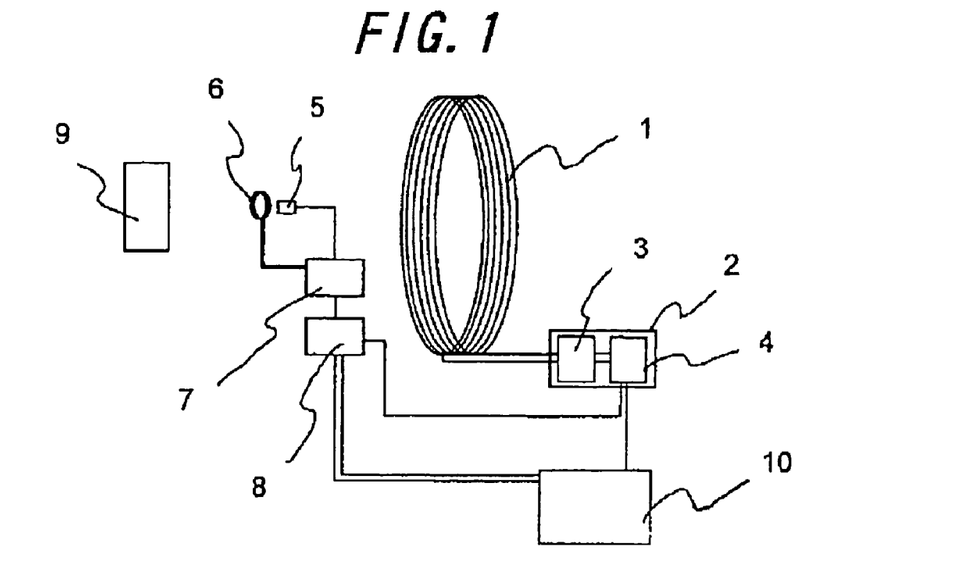
FIG. 1 is a schematic diagram showing a basic configuration of a magnetic detecting device according to the present invention.

FIG. 1 is a schematic diagram showing a basic configuration of a magnetic detecting device according to the present invention. A magnetic field is applied by an apply coil 1 in order to measure a magnetic response of a test object 9. The frequency of the applied magnetic field can be changed by a power source 2 for the apply coil with the use of a signal sender 4. The generated signal drives a current source 3 to apply an alternate current to the apply coil 1. A change in the magnetic field induced by the test object 9 is detected by means of a magnetic sensor 5 comprising a magnetoresistance element. As a matter of course, any one of a magnetic impedance effect sensor, a flux gate, a superconducting quantum interference device can also be used instead. Environmental magnetic noises including the terrestrial magnetism is also input to the magnetic sensor 5, as well as the magnetic field from the test object 9. Not only that, the applied magnetic field is also applied to the magnetic sensor 5. For this reason, a cancel coil 6 for removing other magnetic fields is provided near the magnetic sensor 5 so that only the magnetic field from the test object can be detected. The magnetic sensor 5 is driven with a measurement circuit 7 for the magnetic sensor, and an output thereof is detected by a lock-in amplifier circuit 8. The lock-in amplifier circuit only detects a signal synchronizing the alternate frequency being applied to the apply coil and analyzes the detected signal with an analysis means 10.

Figure 2:
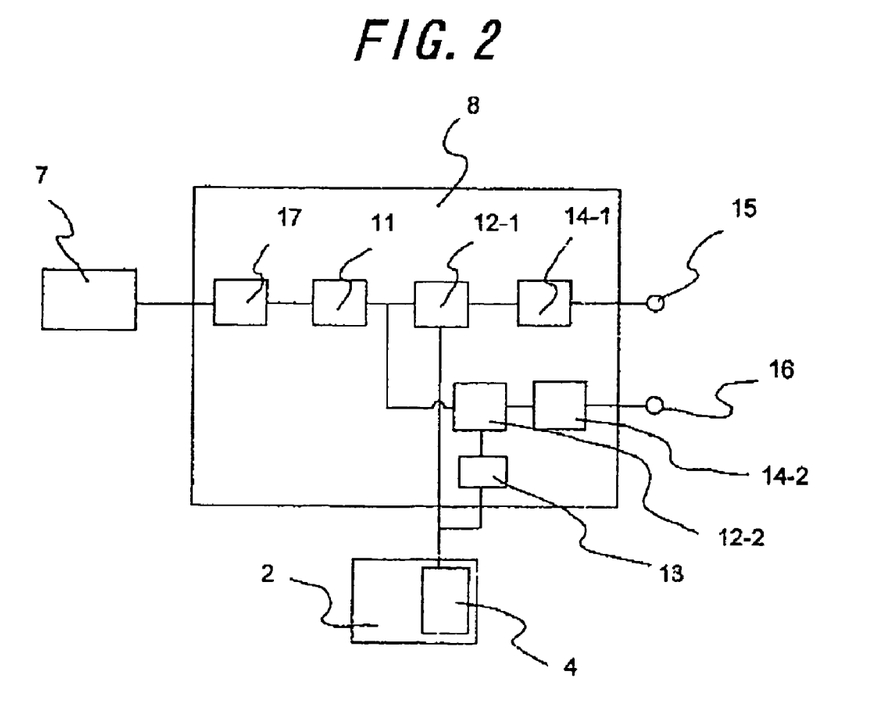
FIG. 2 is a schematic diagram showing a configuration of a lock-in amplifier part of a magnetic detecting device according to the present invention.

FIG. 2 is a schematic diagram showing a configuration of a lock-in amplifier part of a magnetic detecting device according to the present invention. The lock-in amplifier separates a signal having the same phase as that of a signal sender 4 from a signal having a phase shifted by 90 degrees. A direct-current component of an output from the measurement circuit 7 for the magnetic sensor is cut off by a high-pass filter 17 located at a first stage of the lock-in amplifier circuit 8 and amplified by an amplifier 11. The signal is split up into two signals, one of which, a signal having the same phase as that of a signal of the signal sender 4, is detected by a phase detection circuit 12-1 and output to a in-phase output terminal 15 via a low-pass filter 14-1.

The other signal is subject to a 90-degree phase shift 13 and passes through a phase detection circuit 12-2 with a 90-degree shifted phase and is then output to a 90-degree shifted phase output terminal 16 via a low-pass filter 14-2. A magnetic response signal from the test object 9 is thus split off into an in-phase signal and a 90-degree shifted signal. An in-phase signal can be captured for example from a response of a magnetic material; whereas a 90-degree shifted signal is captured for example from an eddy current generated in a metal with high electrical conductivity. Since these signals may vary depending on frequency, the content of the test object 9 can be identified by analyzing frequency changes of the two signals.

Embodiment 2

Figure 3:
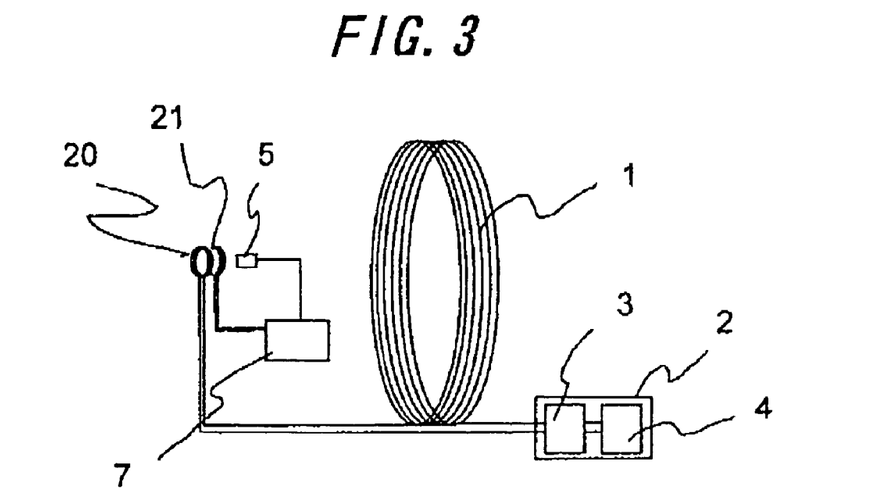
FIG. 3 is a schematic diagram showing a configuration of a coil of a magnetic detecting device according to a second embodiment of the present invention.

FIG. 3 is a schematic diagram showing a configuration of a coil of a magnetic detecting device according to a second embodiment of the present invention. The second embodiment relates to the magnetic detecting device according to the first embodiment, wherein the cancel coil 6 is separated into an apply coil magnetic field cancel coil 20 and a direct magnetic field cancel coil 21, and the apply coil magnetic field cancel coil 20 is connected to the power source 2 for the apply coil with the serially connected apply coil 1. Because the apply coil magnetic field cancel coil 20 and the apply coil 1 are connected in series, magnetic fields generated by the two coils have the same frequency. Consequently, adjustment is not required for the purpose of cancellation.

Embodiment 3

Figure 4:
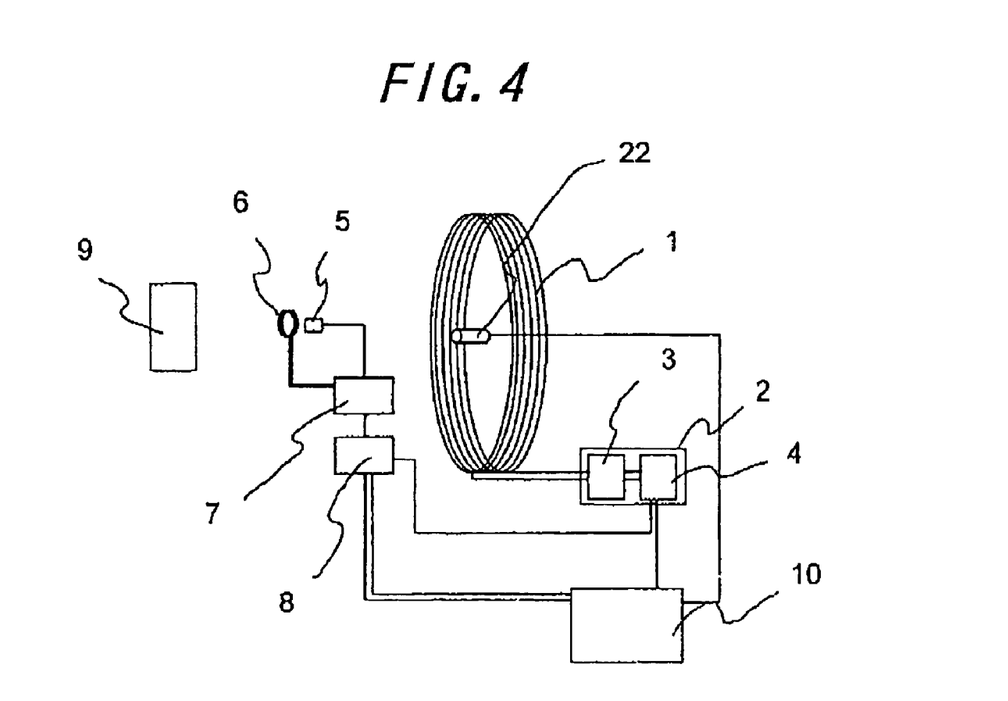
FIG. 4 is a schematic diagram showing a basic configuration of a magnetic detecting device according to a third embodiment of the present invention.

FIG. 4 is a schematic diagram showing a basic configuration of a magnetic detecting device according to a third embodiment of the present invention. In the third embodiment there is provided a distance measurement means 22 for determining positions of the test object 9 and the apply coil 1. The distance measurement means 22 may be placed anywhere, either near the apply coil 1 or the magnetic sensor 5, provided that relative distances between the distance measurement means 22 and both the apply coil 1 and the magnetic sensor 5 are known. A magnetic response from the test object 9 for the applied magnetic field varies according to the distance from the apply coil 1, and the intensity of the signal differs greatly according to the distance from the magnetic sensor 5 for detecting the magnetic response. Thus, measurement can be carried out with higher repeatability by providing the distance measurement means 22.

Figure 5:
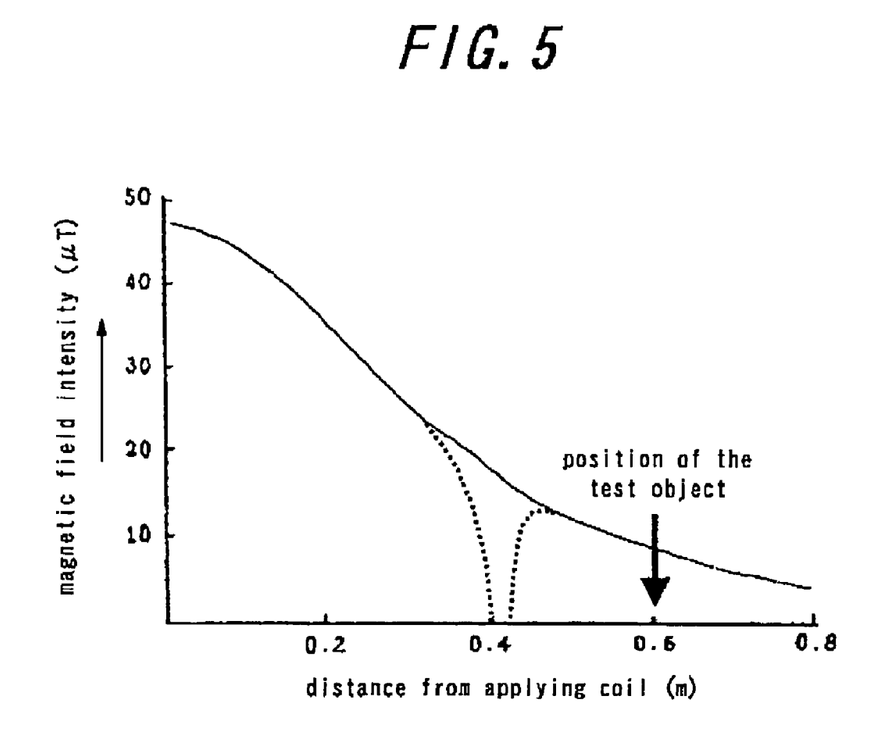
FIG. 5 is a diagram showing a correspondence between the applied magnetic field and the cancel coil magnetic field in the third embodiment.

FIG. 5 is a diagram showing a correspondence between the applied magnetic field and the cancel coil magnetic field in the third embodiment. The diagram shows distance changes of the applied magnetic field and the cancel magnetic field, wherein the area of the cancel coil 6 of the third embodiment is equal to or smaller than a hundredth of that of the apply coil 11. More specifically, the apply coil 1 has a radius 0.4 m, a winding number 40 and a current 1 A, and the cancel coil 6 has a radius 0.015 m, a winding number 1 and a current 1 A. The area ratio in this case is 0.0014, which is roughly a thousandth. With such a small area of the cancel coil 6, the applied magnetic field entering into the magnetic sensor 5 can be cancelled, and influences of the magnetic field generated by the cancel coil 6 around the test object 9 can be removed at the same time. This relation between the areas of the cancel coil and the apply coil is true of all embodiments.

Figure 6:
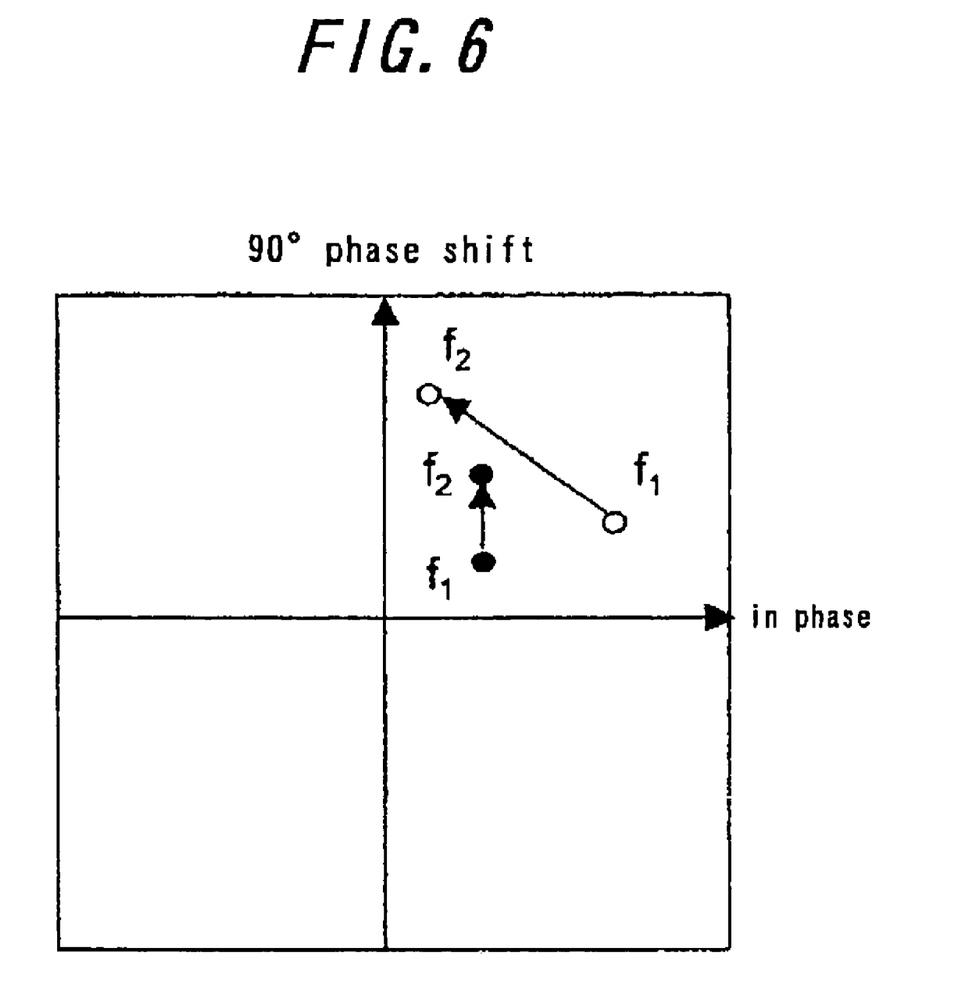
FIG. 6 is a diagram showing a correspondence between each of the two phase output signals and the frequency change in the third embodiment.

FIG. 6 is a diagram showing a correspondence between each of the two phase output signals and the frequency change in the third embodiment. In this figure is plotted a change between results of measurement carried out using frequencies $f_1$ and $f_2$. More specifically, $f_1$ and $f_2$ were 1 kHz and 100 Hz respectively. The white circle represents a result of detection of a test object A, a complex structure comprising iron surrounded by copper. Ferromagnetic properties of iron can be observed in a measurement with low frequency, whereas an effect of an eddy current in the copper body on the surface is large in a measurement with high frequency. The black circle represents a test object B having a double layer structure of electrically conductive metals comprising copper in the center and surrounding aluminum. As to the magnetic response characteristics thereof, no phase change was observed between the cases with high and low frequencies, though there was a change in intensity. In this way, by measuring signals of two different phases using different frequencies, the magnetic characteristics of the test object can be evaluated to identify the object easily.

Embodiment 4

Figure 7:
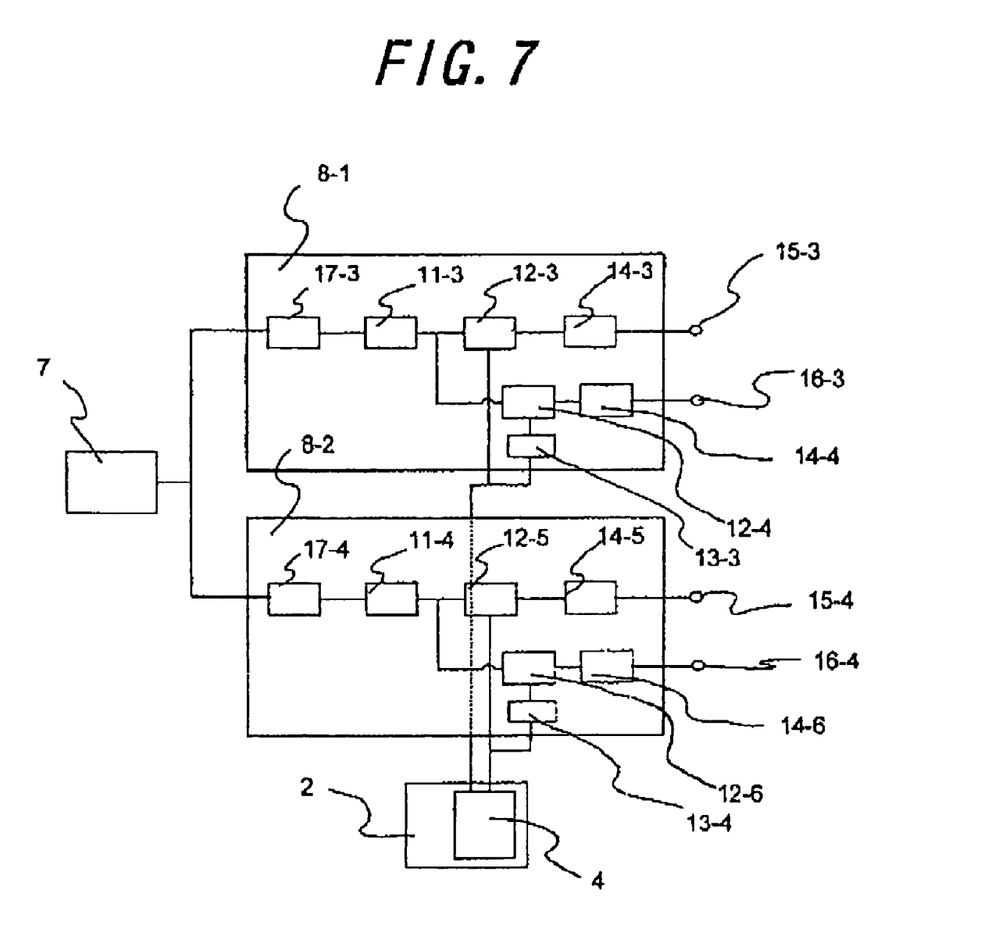
FIG. 7 is a schematic diagram showing a configuration of a lock-in amplifier part of a fourth embodiment, wherein an applied magnetic field is generated by synthesizing two frequencies.

FIG. 7 is a schematic diagram showing a configuration of a lock-in amplifier part of a fourth embodiment, wherein a complex applied magnetic field of two frequencies is used. While measurement was made by switching between frequencies in the third embodiment, in the fourth embodiment, two frequencies are simultaneously generated by a signal sender 4 of the power source 2 for the apply coil, as shown in FIG. 7, and a current wave pattern formed by synthesizing the two frequencies is supplied 10 the apply coil. For this reason, an output from the measurement circuit 7 for the magnetic sensor is split in two, and a lock-in amplifier circuit is provided for each of the frequencies. Thus, there is provided an output terminal for each frequency: in-phase output terminals 15-3, 15-4 and 90-degree shifted phase output terminals 16-3, 16-4. Four signals from these terminals can be obtained simultaneously. With this, phase changes of the magnetic response characteristics of the third embodiment can be measured at once without switching between frequencies.

As for embodiments 1 to 4, magnetic detecting devices comprising a single apply coil were explained. However, when the test object is large or it is necessary to apply a uniform magnetic field to the test object, uniformity of the applied magnetic field is required over a wide range. Additional embodiments will be described below, with which a uniform alternate magnetic field can be applied.

Embodiment 5

Figure 8:
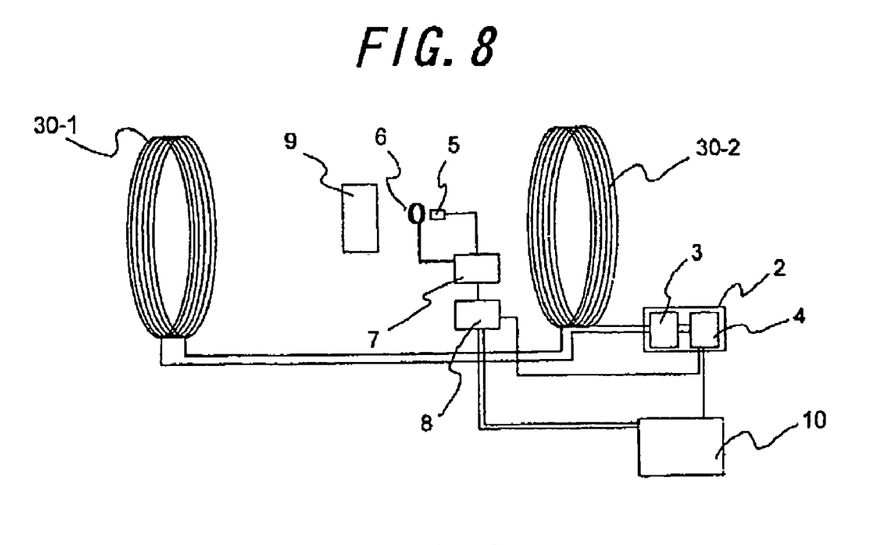
FIG. 8 is a schematic diagram showing a basic configuration of a fifth embodiment of the present invention, wherein facing apply coils are used.

FIG. 8 is a schematic diagram showing a basic configuration of a fifth embodiment of the present invention, wherein a pair of facing apply coil are used. In the fifth embodiment, facing apply coils 30-1 and 30-2 are provided as apply coils, the coil surfaces facing each other. This is a form of combination of coils well-known as a Helmholtz coil, with which magnetic response characteristics of high accuracy can be obtained. Since a magnetic field of greater uniformity can be applied to the test object 9 in the fifth embodiment, a magnetic response can be measured at every part of the test object.

Embodiment 6

Figure 9:
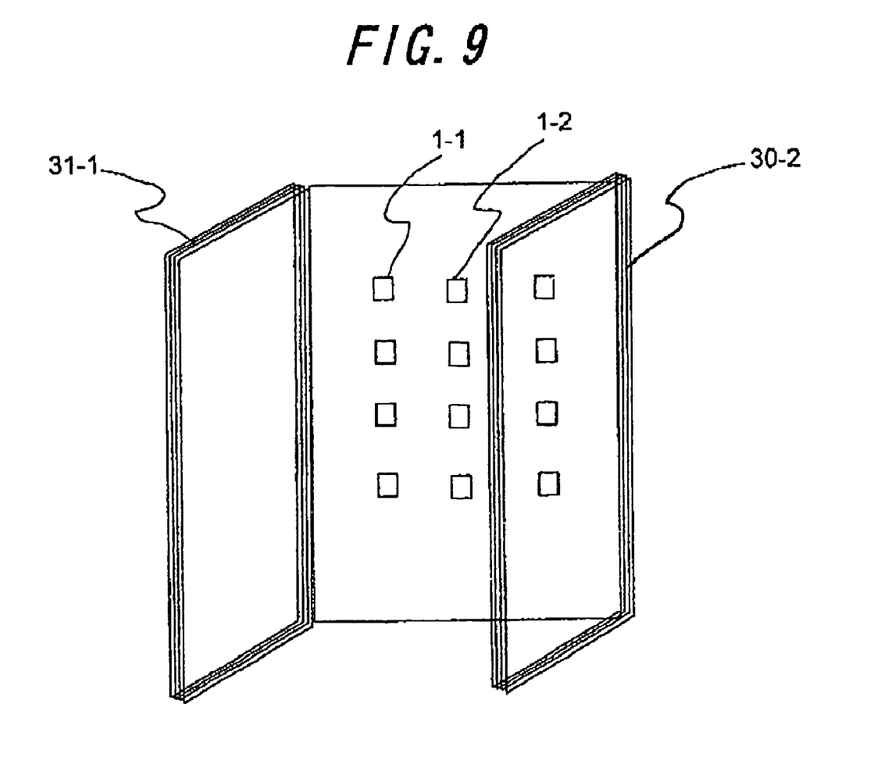
FIG. 9 is a schematic diagram showing a basic configuration of a sixth embodiment of the present invention, wherein facing apply coils and a plurality of magnetic sensors are used.

FIG. 9 is a schematic diagram showing a basic configuration of a sixth embodiment of the present invention, wherein a pair of facing apply coils and a plurality of magnetic sensors are used. In the sixth embodiment, a magnetic response can be measured at each part of the test object with the use of a plurality of magnetic sensors 1. With a greater number of magnetic sensors being provided, a magnetic response can be obtained at more exact position. As the number of magnetic sensors increases, restriction of the position of the test object, which is placed between the coils, becomes more significant.

For this reason, the magnetic sensors are placed on side surfaces of the coil surfaces of the facing apply coils 31-1 and 31-2 in the shape of a rectangle, as shown in FIG. 9, to make much space between the coils. Further, a cancel coil is provided for each of the magnetic sensors, the cancel coil being placed on the back side of each magnetic sensor. Employing facing apply coils in the shape of a rectangle instead of one in the shape of a circle will save space for installation.

The present invention is not limited to the embodiments described above and includes all transformations or design variations within the scope and spirit of the invention.

INDUSTRIAL APPLICABILITY

The present invention relates to a device for applying an alternate magnetic field to a test object and detecting response characteristics thereof by means of a magnetic sensor. Therefore, the device can be used for a metal gate for security check, detection of landmines buried in the ground, detection of foreign matters in food or detection of steel frames buried in concrete. Further, the device can be used even for the purpose of health, such as detection of metal powder having invaded the lung in the case of pneumoconiosis or measurement of current in the body induced when an electromagnetic wave of low frequency is irradiated to a human body.

The invention claimed is:

1. A magnetic detecting device comprising:
   an apply coil for generating an alternate magnetic field of variable frequency and a power source for the apply coil,
   a magnetic sensor for detecting a change in a magnetic field induced by a test object placed at a distance from a surface of said apply coil and toward said test object, said magnetic sensor being provided with a cancel coil for canceling a magnetic field generated at the position of the magnetic sensor by a direct magnetic field and/or said apply coil,
   a measurement circuit for the magnetic sensor for measuring a detection signal of said magnetic sensor,
   a lock-in amplifier circuit for detecting an output of said measurement circuit for the magnetic sensor into two signals having the same frequency as that of said apply coil and phases different from each other by 90 degrees and
   an analysis means for analyzing a phase change of the output of said magnetic sensor using an output signal from said lock-in amplifier circuit.

2. The magnetic detecting device according to claim 1, further comprising a distance measurement means for measuring a distance between said test object and any one of said apply coil or said magnetic sensor.

3. The magnetic detecting device according to claim 1, wherein the area of said cancel coil is made small so as not to influence magnetic detection by said magnetic sensor.

4. The magnetic detecting device according to claim 1, wherein a composite magnetic field of a plurality of frequencies is generated at said apply coil by said power source for the apply coil, and said lock-in amplifier circuit is provided for each of the plurality of frequencies.

5. The magnetic detecting device according to claim 1, wherein a pair of facing apply coils are provided as said apply coil, and said test object is placed between said facing apply coils.

6. The magnetic detecting device according to claim 5, wherein a plurality of said magnetic sensors for measuring a magnetic component in a direction perpendicular to the direction of the axis of said facing apply coils are provided.

7. The magnetic detecting device according to claim 1, wherein any one of a hall element, a magnetoresistive element, a magnetic impedance effect sensor, a flux gate or a superconductive quantum interference device is used as said magnetic sensor.

8. A material identification device for identifying a structure material contained in a test object using the magnetic detecting device according to claim 1.

* * * * *